United States Patent [19]

Esanu

[11] 4,383,998
[45] May 17, 1983

[54] FURO-(3,4-c)-PYRIDINE DERIVATIVES AND THEIR PHARMACEUTICAL USE

[75] Inventor: André Esanu, Paris, France

[73] Assignee: Societe de Conseils de Recherches et D'Applications Scientifiques, Paris, France

[21] Appl. No.: 338,140

[22] Filed: Jan. 8, 1982

[30] Foreign Application Priority Data

Feb. 10, 1981 [GB] United Kingdom ................. 8104072

[51] Int. Cl.³ ................. A61K 31/435; C07D 491/048
[52] U.S. Cl. ..................................... 424/256; 546/116
[58] Field of Search ......................... 546/116; 424/256

[56] References Cited

U.S. PATENT DOCUMENTS 4,221,795 9/1980 Beguin ................................ 424/256

OTHER PUBLICATIONS

Chemical Abstracts 5555f vol. 41 (1947).

*Primary Examiner*—Henry R. Jiles
*Assistant Examiner*—Bernard Dentz
*Attorney, Agent, or Firm*—Eyre, Mann, Lucas & Just

[57] ABSTRACT

This invention relates to new 1,3-dihydro-6-methyl-7-hydroxy-furo-(3,4-c)-pyridine derivatives of the general formula

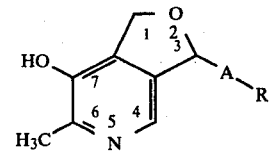

wherein $A<$ represents a group of the formula $-(CH_2)_n-$, n being an integer of from 1 to 5, or a homocyclic or heterocyclic group, and R represents a hydrogen, chlorine or fluorine atom, a trifluoromethyl group, an alkyl group having from 1 to 5 carbon atoms, an alkoxy group having from 1 to 5 carbon atoms, a alkylthio group having from 1 to 5 carbon atoms, a dialkylaminoalkoxy group in which the alkyl groups each have from 1 to 5 carbon atoms and the alkoxy group has from 1 to 5 carbon atoms or a N-pyrolidinyl-alkoxy group in which the alkoxy group has from 1 to 5 carbon atoms to a process for the preparation of the same by refluxing $\alpha^4$, 3-o-isopropylidene-pyridoxal with a compound of the general formula X-A-R, wherein X represents a bromine or iodine atom, in the presence of magnesium in diethyl ether, and acidifying the resultant corresponding secondary alcohol $\alpha^4$, 3-o-isopropylidene-$\alpha$-hydroxy-5-substituted-pyridoxine to break the isopropylidene ring and promote a 3,4 cyclization; and to therapeutical compositions of matter comprising as an essential ingredient therein an effective amount of one of these compounds.

2 Claims, No Drawings

FURO-(3,4-c)-PYRIDINE DERIVATIVES AND THEIR PHARMACEUTICAL USE

The invention relates to furo-(3,4-c)-pyridine derivatives, to a process for their preparation and to therapeutical composition containing the same.

The invention provides 1,3-dihydro-6-methyl-7-hydroxyfuro-(3,4-c)-pyridine derivatives of the general formula I

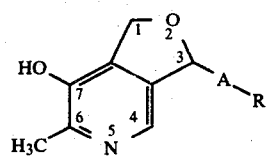

wherein A< represents a group of the formula —(CH$_2$)$_n$—, n being an integer of from 1 to 5, or a homocyclic or heterocyclic group, and R represents a hydrogen, chlorine or fluorine atom, a trifluoromethyl group, an alkyl group having from 1 to 5 carbon atoms, an alkoxy group having from 1 to 5 carbon atoms, a alkylthio group having from 1 to 5 carbon atoms, a dialkylaminoalkoxy group in which the alkyl groups each have from 1 to 5 carbon atoms and the alkoxy group has from 1 to 5 carbon atoms or a N-pyrolidinyl-alkoxy group in which the alkoxy group has from 1 to 5 carbon atoms.

The compounds according to the invention are of interest for their therapeutical activity, principally in the fields of diuresis and of the lowering of blood pressure.

The invention further provides a process for the preparation of 1,3-dihydro-6-methyl-7-hydroxy-furo-(3,4-c)-pyridine derivatives of the general formula I, the process comprising refluxing $\alpha^4$, 3-o-isopropylidene-pyridoxal with a compound of the general formula X-A-R, wherein A and R have the meanings ascribed to them above and X represents a bromine or iodine atom, in the presence of magnesium in diethyl ether, and acidifying the resultant corresponding secondary alcohol $\alpha^4$, 3-o-isopropylidene-$\alpha$-hydroxy-5-substituted-pyridoxine to break the isopropylidene ring and promote a 3,4 cyclisation. The process is exemplified by the following reaction sequence:

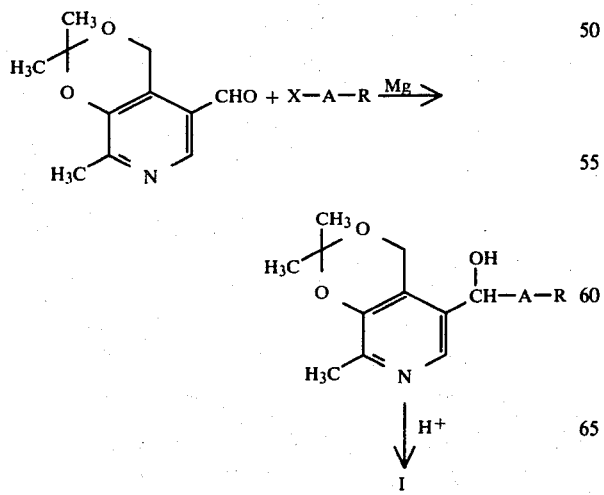

The starting $\alpha^4$, 3-o-isopropylidene-pyridoxal may be obtained by oxidation, using manganese dioxide, of $\alpha^4$, 3-o-isopropylidene-pyridoxine itself obtained from pyridoxine by the method described in British Patent Specification No 1,286,161.

The invention is illustrated by the following Examples:

EXAMPLE 1

1,3-dihydro-3,6-dimethyl-7-hydroxy-furo-[3,4-c]-pyridine

In a 3 liter reactor having stirring, warming and cooling means, and previously having been flushed with nitrogen, were placed 9.7 g (0.4 mol) of magnesium. 56.8 g (0.4 mol) of methyl iodide dissolved in 600 ml of distilled diethyl ether was poured slowly into the reactor, stirring continuously. The mixture was refluxed for 2 to 3 hours and then cooled to 10°–15° C. 62.1 g (0.3 mol) of $\alpha^4$, 3-o-Isopropylidene-pyridoxal dissolved in 600 ml of distilled diethyl ether were slowly added. The mixture was stirred for 12 hours at room temperature and then the diethyl ether was evaporated off under reduced pressure. After cooling, there were added 1 liter of chloroform and, dropwise, under stirring, 125 ml of 2 N hydrochloric acid. Stirring was maintained for 2 hours and the liquid was then decanted off. The precipitate was washed with water, dried on anhydrous sodium sulphate, redissolved in diisopropyl ether, recrystallized, washed and dried.

The compound thus obtained was then treated (second step) with 500 ml of concentrated hydrochloric acid at room temperature, under stirring, for 12 hours. The precipitate obtained was treated twice with ethanol and recrystallized from acetone. Yield: 46.6 g (77%) of a beige product melting at 167° C. (Tottoli), elemental analysis of which showed good correspondence with the formula $C_9H_{11}NO_2,HCl$. The compound had good solubility in water at room temperature.

EXAMPLE 2

1,3-dihydro-3-ethyl-6-methyl-7-hydroxy-furo-[3,4-c]-pyridine

This compound was obtained by the method described in Example 1, but replacing the methyl iodide by ethyl iodide (62.4 g, 0.4 mol). Yield 46 g (71%) of a white product melting at 172° C. (Tottoli), elemental analysis of which showed good correspondence with the formula $C_{10}H_{13}NO_2,HCl$. The compound had very good solubility in water at room temperature.

EXAMPLE 3

1,3-dihydro-3-propyl-6-methyl-7-hydroxy-furo-[3,4-c]-pyridine

This compound was obtained by the method described in Example 1, but replacing the methyl iodide by propyl bromide (49.2 g, 0.4 mol). Yield: 55.8 g (81%) of a beige product melting at 160° C. (Tottoli), elemental analysis of which showed good correspondence with the formula $C_{11}H_{15}NO_2,HCl$. The compound had moderate solubility in water at room temperature.

EXAMPLE 4

1,3-dihydro-3-phenyl-6-methyl-7-hydroxy-furo-[3,4-c]-pyridine

This compound was obtained by the method described in Example 1, from 7.9 g (0.325 mol) of magnesium, 51 g (0.325 mol) of phenyl bromide and 51.8 g (0.25 mol) of $\alpha^4$, 3-o-isopropylidene-pyridoxal. Yield: 46.1 g (70%) of a white powder melting at 205°–209° C. (Tottoli), elemental analysis of which showed good correspondence with the formula $C_{14}H_{13}NO_2$,HCl. The compound had good solubility in water at room temperature.

EXAMPLE 5

1,3-dihydro-3-p-chlorophenyl-6-methyl-7-hydroxy-furo-[3,4-c]-pyridine

This compound was obtained by the method described in Example 1, from 6.3 g (0.26 mol) of magnesium, 49.8 g (0.26 mol) of p-chlorophenyl bromide and 41.4 g (0.20 mol) of $\alpha^4$, 3-o-isopropylidene-pyridoxal. Yield: 50.1 g (84%) of a white crystalline product melting at 219°–228° C. (Tottoli), elemental analysis of which showed good correspondence with the formula $C_{14}H_{12}ClNO_2$,HCl. The compound was insoluble in water.

EXAMPLE 6

1,3-dihydro-3-p-trifluoromethylphenyl-6-methyl-7-hydroxy-furo-[3,4-c]-pyridine

This compound was obtained by the method described in Example 1, but replacing the methyl iodide by p-trifluoromethylphenyl bromide (90 g, 0.4 mol). Yield: 76.6 g (77%) of a white crystalline product melting at 220°–223° C. (Tottoli), elemental analysis of which showed good correspondence with the formula $C_{15}H_{12}F_3NO_2$,HCl. The compound was insoluble in water at room temperature.

EXAMPLE 7

1,3-dihydro-3-m-trifluoromethylphenyl-6-methyl-7-hydroxy-furo-[3,4-c]-pyridine

This compound was prepared by the method described in Example 6, from m-trifluoromethylphenyl bromide. Yield: 73.6 g (74%) of a white crystalline product melting at 206°–207° C. (Tottoli). The compound was insoluble in water at room temperature.

EXAMPLE 8

1,3-dihydro-3-p-methoxyphenyl-6-methyl-7-hydroxy-furo-[3,4-c]-pyridine

This compound was obtained by the method described in Example 1, but replacing the methyl iodide by p-methoxyphenyl bromide (74.8 g, 0.4 mol). Yield: 59 g (67%) of a white crystalline product melting at 215° C. with decomposition, elemental analysis of which showed good correspondence with the formula $C_{15}H_{15}NO_3$,HCl. The compound was insoluble in water at room temperature.

EXAMPLE 9

1,3-dihydro-3-p-methylthiophenyl-6-methyl-7-hydroxy-furo-[3,4-c]-pyridine

This compound was obtained by the method described in Example 1, but replacing the methyl iodide by p-thiomethylphenyl bromide (81.2 g, 0.4 mol). Yield: 58.5 g (63%) of a pink product melting at 210°–220° C. with decomposition, elemental analysis of which showed good correspondence with the formula $C_{15}H_{15}NO_2S$,HCl. The compound was insoluble in water at room temperature.

EXAMPLE 10

1,3-dihydro-3-(p-dimethylaminoethoxy)phenyl-6-methyl-7-hydroxy-furo-[3,4-c]-pyridine This compound was obtained by the method described in Example 1, from 5.05 g (0.208 mol) of magnesium, 50.75 g (0.208 mol) of p-dimethylaminoethoxyphenyl bromide and 36 g (0.174 mol) of $\alpha^4$, 3-o-isopropylidene-pyridoxal. Yield: 36.1 g (66%) of a beige powder melting at 178°–185° C. (Tottoli), elemental analysis of which showed good correspondence with the formula $C_{18}H_{22}N_2O_3$. The compound was insoluble in water at room temperature.

EXAMPLE 11

1,3-dihydro-3-(p-diethylamino-ethoxy)phenyl-6-methyl-7-hydroxy-furo-[3,4-c]-pyridine This compound was obtained by the method described in Example 1, from 9.7 g (0.4 mol) of magnesium, 108.8 g (0.4 mol) of p-diethylaminoethoxyphenyl bromide and 62.1 g (0.3 mol) of $\alpha^4$, 3-o-isopropylidene-pyridoxal. Yield: 75 g (73%) of a white crystalline product melting at 179°–180° C. (Tottoli), elemental analysis of which showed good correspondence with the formula $C_{20}H_{26}N_2O_3$. The compound was insoluble in water at room temperature.

EXAMPLE 12

1,3-dihydro-3-(p-pyrrolidinylethoxy)-phenyl-6-methyl-7-hydroxy-furo-[3,4-c]-pyridine This compound was obtained by the method described in Example 1, from 9,7 g (0.4 mol) of magnesium, 108 g (0.4 mol) of p-pyrrolidinylethoxy phenyl bromide and <62.1 g (0.3 mol) of $\alpha^4$, 3-o-isopropylidene-pyridoxal. Yield: 98 g (79%) of a beige powder melting at 215° C. (Kofler), elemental analysis of which showed good correspondence with the formula $C_{20}H_{24}N_2O_3$, 2HCl. The compound had good solubility in water at room temperature.

EXAMPLE 13

1,3-dihydro-3-α-thienyl-6-methyl-7-hydroxy-furo-3,4-c-pyridine

This compound was obtained by the method described in Example 1, from 4.74 g (0.195 mol) of magnesium, 31.8 g (0.195 mol) of α-bromothiophene and 31 g (0.15 mol) of $\alpha^4$,3-o-isopropylidene-pyridoxal. Yield: 25.1 g (62%) of a beige powder melting at 190° C. (Tottoli), elemental analysis of which showed good correspondence with the formula $C_{12}H_{11}NO_2S$, HCl. The compound was slightly soluble in water at room temperature.

TOXICITY

The toxicity of the compounds according to the invention has been determined on rats and mice, by oral route. For the rats no LD 50 could be found for no death was noticed at the dose of 5 g/kg. For the mice the LD 50 for the more toxic compound (example 12) was 4.2 g/kg.

A sub-acute toxicity study was undertaken on rats and dogs at the doses of 10,60 and 360 mg/kg for six weeks by oral route: neither death was noticed nor any variation of the measurable factors.

PRESENTATION

The preferred mode of administration includes tablets and gelatine capsules; for tablets the dosage units comprise 50 or 100 mg of active ingredient together with an appropriate carrier, such as, for instance, starch.

POSOLOGY

In human therapy it is generally advisable to administer 100 to 400 mg per diem for at least one week and, more generally, two or three weeks.

PHARMACOLOGY

The interest of the compounds of the invention has been evidenced by various pharmacologic tests.

(1) Study of the urinary elimination in the rat.

This study has been conducted on Wistar male rats weighing 270–280 g.

Eight batches of each eight animals were used; six batches by the compounds according to the invention, one batch by tienilic acid as reference compound, all animals of these seven batches at the same dose of 50 ml/kg/day; the eighth batch is for control.

The animals were treated for three days and placed in a metabolic cage fitted for the collection of urines; neither food nor drink was given during the treatment in order to avoid any contamination. The collected volumes of urine are measured after six hours and twenty four hours. After six hours, each animal receives 25 ml/kg of physiologic serum. On the fourth day, the animal receives a last treatment and blood is taken off at the retro orbital sinus under slight anaesthesia by diethyl ether. The results are reported in the table 1.

(2) Action on blood pressure.

This study was conducted on rats suffering from induced high blood pressure, by the method of GOLD-BLATT in comparison with Indapamine. This method is no longer described, for it is well known and the study shows, at the same therapeutic doses, that the compounds of the invention have, on this test, the same action for the lowering of blood pressure on the rats.

(3) Action on an experimental hyper lipemia on rabbit.

This study has been conducted according to the method of C. B. AMMERMAN and Coll.; Am. J. PHYS. (1961) 200, 75–79.

In this method, the suppression of drink for five days, induces in the rabbit a higher hepatic bio-synthesis of cholesterol. Blood is taken off after the sixth day in the abdominal aorta for the dosage of total lipids, triglycerids, total cholesterol, HDL cholesterol (enzymatic method after electrophoresis on cellulose acetate).

The livers are taken off and weighted. In all the cases the administration was done directly in the oesophagus from the third to the fifth days. This experimentation has been conducted simultaneously on batches of six animals, two control batches (normal control and control without food), one reference batch (animal without food but treated by tienilic acid) and the last three batches by three of the compounds of the invention). These four last batches receive 50 ml/kg/day. The results are reported in table 2.

In conclusion of the various experimentations it can be noticed that the compounds of the invention have a regular diuretic action slightly better than the known diuretics of the same clinical family (thiazidic). They have also an action on the lowering of blood pressure which is rather common in diuretics. However, the most important fact is a significant lowering of the lipid rates in blood: this is a highly favorable action, for the patients treated by diuretics are generally suffering also from arteriosclerosis or other circularly insufficiencies wherein the lowering of the lipid rates is highly desired. For this reason, the compounds of the invention may be considered as diuretics offering a better protection of the patient, and preclinical experimentations have confirmed the reality and the interest of this action.

TABLE 1

| Administration per os of | Volumes (ml) | | |
|---|---|---|---|
| 50 mg/kg/day | 0–6 h | 6–24 h | 0–24 h |
| Control | 5.6 | 14.2 | 19.8 |
| Tienilic acid | 7.9 | 8.5 | 16.5 |
| Ex. 1 | 9.5 | 10.8 | 20.3 |
| Ex. 3 | 10.1 | 10.6 | 20.7 |
| Ex. 5 | 10.4 | 10.8 | 21.3 |
| Ex. 8 | 10.1 | 10.6 | 20.7 |
| Ex. 10 | 9.8 | 11.0 | 20.8 |
| Ex. 13 | 8.9 | 11.3 | 20.2 |

TABLE 2

| | Weight of livers g./l. | Plasmatic values | | | Cholesterol of the lipoproteins | | Total cholesterol HDL choles- terol g./l. |
|---|---|---|---|---|---|---|---|
| | | Total lipids g./l. | Triglycerids g./l. | Total cholesterol g./l. | HDL cholesterol g./l. | LDL cholesterol g./l. | |
| Control | 3.48 | 5.22 | 1.71 | 0.79 | 0.18 | 0.31 | 4.69 |
| Control without food | 2.55 | 11. | 1.19 | 2.63 | 0.38 | 2.10 | 6.85 |
| Tienilic acid | 2.84 | 12.34 | 2.02 | 2.51 | 0.22 | 1.73 | 15.99 |
| Ex. 1 | 2.66 | 11.10 | 1.60 | 2.49 | 0.27 | 1.65 | 8.24 |
| Ex. 5 | 2.76 | 11.39 | 1.45 | 2.50 | 0.31 | 1.67 | 7.71 |
| Ex. 8 | 2.69 | 11.92 | 1.51 | 2.46 | 0.32 | 1.67 | 8.01 |

I claim:

1. A 1,3-dihydro-6-methyl-7-hydroxy-furo-(3,4-c)-pyridine derivative of the general formula

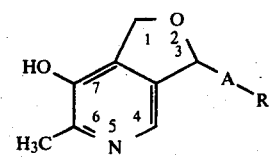

wherein A< represents a group of the formula —(CH$_2$)$_n$—, n being an integer of from 1 to 5, or a phenyl or thienyl group, and R represents a hydrogen, chlorine or fluorine atom, a trifluoromethyl group, an alkyl group having from 1 to 5 carbon atoms, an alkoxy group having from 1 to 5 carbon atoms, a thioalkyl group having from 1 to 5 carbon atoms, a dialkylaminoalkoxy group in which the alkyl groups each have from 1 to 5 carbon atoms and the alkoxy group has from 1 to 5 carbon atoms or a N-pyrolidinyl-alkoxy group in which the alkoxy group has from 1 to 5 carbon atoms.

2. A composition for effecting diuresis and the lowering of the lipid rates in blood comprising a therapeutically effective amount of at least one of the compounds of claim 1 in a therapeutically acceptable carrier therefor.

* * * * *